US012626463B2

(12) United States Patent
Razavizadeh

(10) Patent No.: US 12,626,463 B2
(45) Date of Patent: May 12, 2026

(54) SYSTEM AND METHOD FOR GENERATING A VIRTUAL MODEL OF A VIRTUAL PATIENT

(71) Applicant: Siemens Healthineers AG, Forchheim (DE)

(72) Inventor: Seyedsina Razavizadeh, Bamberg (DE)

(73) Assignee: Siemens Healthineers AG, Forchheim (DE)

( * ) Notice: Subject to any disclaimer, the term of this patent is extended or adjusted under 35 U.S.C. 154(b) by 149 days.

(21) Appl. No.: 18/608,093

(22) Filed: Mar. 18, 2024

(65) Prior Publication Data

US 2025/0292504 A1     Sep. 18, 2025

(30) Foreign Application Priority Data

Mar. 8, 2023     (EP) ..................................... 23160698

(51) Int. Cl.
| | |
|---|---|
| *G06T 17/20* | (2006.01) |
| *G06T 19/20* | (2011.01) |
| *G16H 30/20* | (2018.01) |

(52) U.S. Cl.
CPC .............. *G06T 17/20* (2013.01); *G06T 19/20* (2013.01); *G06T 2200/24* (2013.01);
(Continued)

(58) Field of Classification Search
CPC ... A61B 34/25; A61B 34/10; A61B 2034/256; A61B 2034/101; A61B 2090/3764;
(Continued)

(56) References Cited

U.S. PATENT DOCUMENTS

| | | | |
|---|---|---|---|
| 12,213,774 B1 * | 2/2025 | Aravamudan ......... | G16H 50/50 |
| 2005/0018885 A1 * | 1/2005 | Chen ...................... | G06T 17/00 |
| | | | 382/128 |

(Continued)

FOREIGN PATENT DOCUMENTS

| | | | | |
|---|---|---|---|---|
| CN | 113053194 A | 6/2021 | | |
| EP | 4428875 A1 * | 9/2024 | ............. | G06T 19/20 |

OTHER PUBLICATIONS

Prassl AJ, Kickinger F, Ahammer H, Grau V, Schneider JE, Hofer E, Vigmond EJ, Trayanova NA, Plank G. Automatically generated, anatomically accurate meshes for cardiac electrophysiology problems. IEEE Transactions on Biomedical Engineering. Feb. 6, 2009; 56(5):1318-30.*

(Continued)

*Primary Examiner* — Phu K Nguyen
(74) *Attorney, Agent, or Firm* — Harness, Dickey & Pierce, P.L.C.

(57)     ABSTRACT

A system for generating a virtual model of a virtual patient including: a template module to provide a morphable virtual 3D mesh template for a virtual model of a human organ; an anatomical parameters module to provide a range of values for each adjustable anatomical parameters of the virtual model, each value associated with a morphed state of the template; a plausibility module to provide at least one relation for the template in at least one morphed state, the relation being between at least two of the parameters; an instantiation module to provide, using a pseudo-random number generator, a parameter set including, for each parameter of the virtual model, a value of the corresponding range of values, while fulfilling the at least one relation; and a generating module to generate the virtual model based on the template in the morphed state corresponding to the selected parameters.

17 Claims, 4 Drawing Sheets

(52) U.S. Cl.
  CPC ...... *G06T 2210/41* (2013.01); *G06T 2210/44* (2013.01); *G06T 2219/2021* (2013.01); *G16H 30/20* (2018.01)

(58) Field of Classification Search
  CPC ........ A61B 2090/365; A61B 2034/105; G06T 17/20; G06T 19/20; G06T 2210/44; G06T 2219/2021; G06T 2200/24; G06T 2210/41; G16H 50/20; G16H 50/50; G16H 50/70; G16H 30/20; G06N 20/00
  USPC ........................................................ 345/418
  See application file for complete search history.

(56) References Cited

U.S. PATENT DOCUMENTS

| | | | |
|---|---|---|---|
| 2015/0055086 A1* | 2/2015 | Fonte ..................... | G02C 7/024 |
| | | | 700/98 |
| 2021/0088811 A1* | 3/2021 | Varady ................. | G06V 40/171 |
| 2022/0276511 A1* | 9/2022 | Varady ................. | G06V 40/171 |
| 2023/0149091 A1* | 5/2023 | Cohen-Gadol ......... | G06T 15/08 |
| | | | 606/1 |
| 2025/0117929 A1* | 4/2025 | Barve ................... | G06T 7/0012 |

OTHER PUBLICATIONS

Lorenz C, von Berg J. A comprehensive shape model of the heart. Medical image analysis. Aug. 1, 2006;10(4):657-70.*

Lazarus A. Surrogate modelling of a patient-specific mathematical model of the left ventricle in diastole (Doctoral dissertation, University of Glasgow).*

Materialize Medical, How to Create a Heart Model for 3D Printing | Mimics Innovation Suite | Materialise Medical, Aug. 14, 2017, https://www.youtube.com/watch?v=j-Z_R8sapro.*

Tinker This Education, 3D modeling a Human Heart in TinkerCAD (Dissection). 3D printing, May 4, 2021, https://www.youtube.com/watch?v=IZLYX96ZdEc&list=PLzASd_InZL9ns1AVympyVFjYKirmei2ob.*

Doost SN, Ghista D, Su B, Zhong L, Morsi YS. Heart blood flow simulation: a perspective review. Biomedical engineering online. Aug. 25, 2016;15(1):101.*

Unknown: "Physiome Project: Home", Dec. 5, 2022 (Dec. 5, 2022), pp. 1-2, XP93064417, Retrieved from the Internet: URL: https%3A%2F%2Fweb.archive.org%2Fweb%2F20221205100857%2Fhttps%3A%2F%2Fphysiomeproject.org%2F.

Kivi, Petrus E. J. et al:"Real-Time Rendering of Point Clouds With Photorealistic Effects: A Survey", Digital Object Identifier 10.1109/ACCESS.2022.3146768, Screenshot: Nov. 10, 2022, https://ieeexplore.ieee.org/document/9693528.

Szirmay-Kalos L., et al.: "Displacement Mapping on the GPU—State of the Art", Wiley One Library, vol. 27, Issue6, Sep. 2008, pp. 1567-1592 https://onlinelibrary.wiley.com/doi/abs/10.1111/j.1467-8659.2007.01108.x.

Windecker St. et al.:"Which patients with aortic stenosis should be referred to surgery rather than transcatheter aortic valve implantation?", European Heart Journal (2022) 43, 2729-2750, (https://academic.oup.com/eurheartj/article/43/29/2729/6572863).

Imai, Norio et al: "Evaluation of anatomical pelvic parameters between normal, healthy men and women using three-dimensional computed tomography: a cross-sectional study of sex-specific and age-specific differences", Journal of Orthopaedic Surgery and Research, [Online] vol. 14, No. 1, May 9, 2019 (May 9, 2019), XP93064420, DOI: 10.1186/s13018-019-1165-2 Retrieved from the Internet: URL:http://link.springer.com/article/10.1186/s13018-019-1165-2/fulltext.html>.

Drive medical research, education, and training; The Pulse Physiology Engine; https://pulse.kitware.com/, Jul. 17, 2023.

Lorensen et.al., Marching Cubes: A high resolution 3D surface construction algorithm; ACM Siggraph Computer Graphics, vol. 21, No. 4, pp. 163-169, Jul. 1987.

De Oliveira, Julia E. E. et al: "Surface mesh to voxel data registration for patient-specific anatomical modeling", Progress in Biomedical Optics and Imaging, SPIE—International Society for Optical Engineering, Bellingham, WA, US, vol. 9786, Mar. 18, 2016 (Mar. 18, 2016), pp. 978625-978625, XP060069366, ISSN: 1605-7422, DOI: 10.1117/12.2217491 ISBN: 978-1-5106-0027-0.

* cited by examiner 20, 30

34

32

S100

S200

S300

S400

S500

S600

S700

S800

S900

450

400

550

500

SYSTEM AND METHOD FOR GENERATING A VIRTUAL MODEL OF A VIRTUAL PATIENT

CROSS-REFERENCE TO RELATED APPLICATION(S)

The present application claims priority under 35 U.S.C. § 119 to European Patent Application No. 23160698.9, filed Mar. 8, 2023, the entire contents of which is incorporated herein by reference.

FIELD

One or more example embodiments of the present invention relates to a computer-implemented system for generating a virtual model of a virtual patient, in particular a virtual model of at least a part of an organ of the virtual patient, and more particular to a virtual model of a heart of the virtual patient. One or more example embodiments of the present invention also relates to a computer-implemented method for generating such a virtual model, to a computer-implemented method for generating a training data set for machine learning, to a computer program, to a data storage medium, and to a data stream.

RELATED ART

Virtual models, displayed in graphical user interfaces, can contribute to training physicians or other medical personnel. To fulfil the training goals of interventional cardiology procedures (e.g. PCI and TAVR), simulation devices have been introduced that provide virtual patient models. These models are created from real patient datasets to maintain as realistic of an experience as possible.

However, due to limited access to complete patient datasets, the number of these virtual models is limited, and the model itself is bound to the physiological properties of the real patient. This, in turn, leads to limited training scenarios and complications that the user of these devices can experience, hence reducing the long-term engagement with the system and achieving the training goals.

In addition, creating these models one by one is a long and arduous task, which requires a team of specialized experts to accomplish, and adds further costs to the development process. Furthermore, these datasets are in the grace of their providers (i.e. patients) and can be removed on their demand, rendering the development efforts futile. Data privacy regulations such as the European GDPR further limit the ways in which real patient data can be freely used to generate additional virtual patient models.

Also known are physiology engines, which simulate physiological processes based on virtual models. One such physiology engine is the Pulse Physiology engine 4.1.0 (registered trademark) available under http://pulse.kitware-.com/. However, without a large variety of virtual models, and a method for generating such virtual models cost-effectively, the known physiology engines have only limited use cases in training physicians or other medical specialists.

Known in the prior art are also methods of rendering 3-dimensional virtual models and of changing their shape, for example surface rendering methods as described in the scientific publication by L. Szirmay-Kalo and T. Umenhoffer, "Displacement Mapping on the GPU—State of the Art", https://onlinelibrary.wiley.com/doi/abs/10.1111/ j.1467-8659.2007.01108.x (hereafter cited as "Szirmay-Kalo/Umenhoffer").

Other methods for generating 3-dimensional virtual models include point-cloud rendering techniques such as described in the scientific publication by P. Kivi et al, "Real-Time Rendering of point Clouds with Photorealistic Effects: A Survey", https://ieeexplore.ieee.org/document/ 9693528, DOI: 10.1109/ACCESS.2022.3146768, hereafter cited as "Kivi et al.". This publication reviews real-time photorealistic point cloud rendering methods, which directly ray trace or rasterize point cloud models, with an emphasis on ray tracing and real-time performance.

Further, for the training of artificial intelligence entities such as artificial neural networks or the like, usually training data are of the essence. Access to a large number of virtual patient models therefore enables improved training of artificial intelligence entities.

SUMMARY

One or more example embodiments of the present invention provides an improved system for generating a virtual model of a patient, and a further objective to provide an improved method for generating such a model. One or more example embodiments of the present invention provides an improved method for generating training data for machine learning, and providing a computer program product, a data storage medium and a data stream for implementing any of the improved methods.

BRIEF DESCRIPTION OF THE DRAWINGS

The accompanying drawings are included to provide a further understanding of the present invention and are incorporated in and constitute a part of this specification. The drawings illustrate embodiments of the present invention and together with the description serve to explain the principles of the invention. Other embodiments of the present invention and many of the intended advantages of the present invention will be readily appreciated as they become better understood by reference to the following detailed description. The elements of the drawings are not necessarily to scale relative to each other. Like reference numerals designate corresponding similar parts.

In the figures.

DETAILED DESCRIPTION

Figure 1:
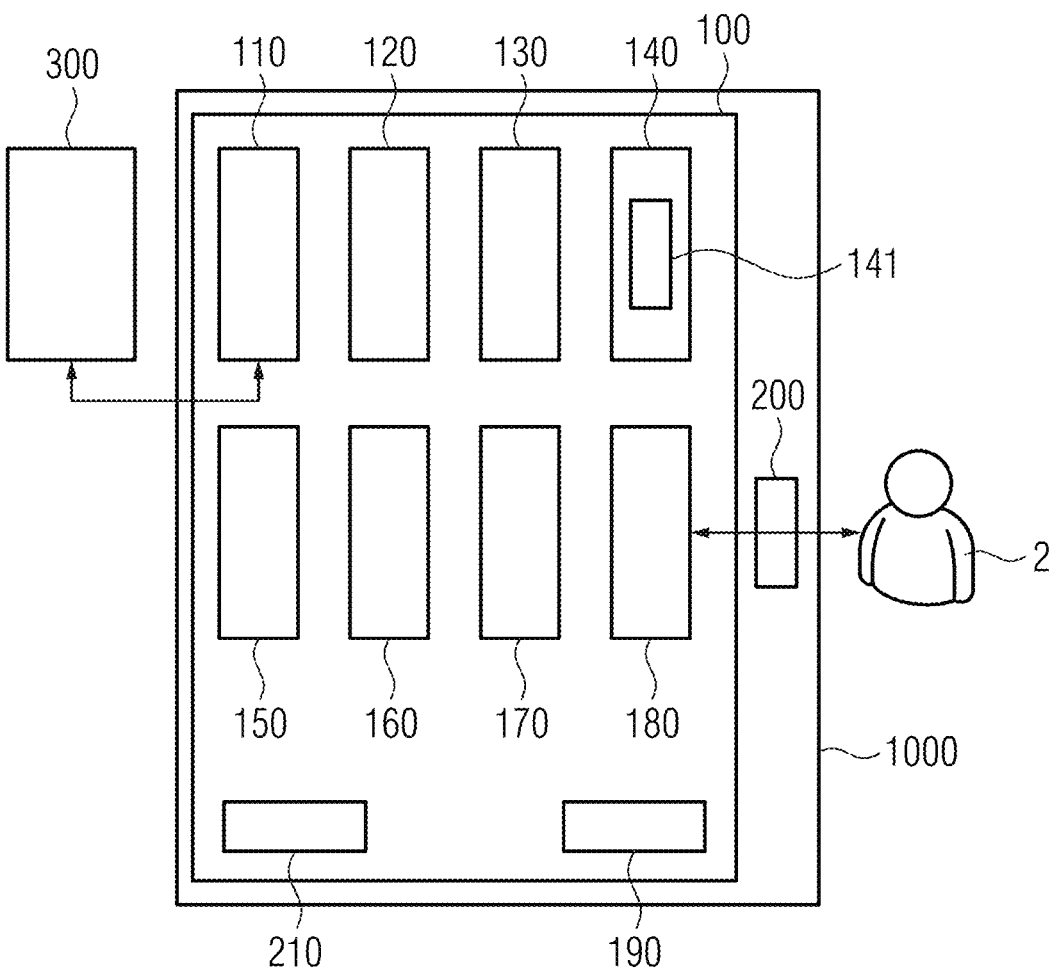
FIG. 1 shows a schematic block diagram illustrating a system for generating a virtual model of a virtual patient according to an embodiment of the present invention.

Accordingly, according to one or more example embodiments of the present invention, a computer-implemented system for generating a virtual model of a virtual patient is provided. The system comprises:

a computing device configured to implement:

a template module configured to provide a morphable virtual 3D mesh as a template for a virtual model of at least a part of a human organ;

an anatomical parameters module, APM, configured to provide a range of values for each of a plurality of adjustable anatomical parameters, AAP, of the virtual model, each value associated with a corresponding morphed state of the template;

a plausibility module configured to provide at least one relation to be fulfilled by the template in at least one morphed state, the relation being between at least two of the plurality of adjustable anatomical parameters, AAP;

an instantiation module configured to provide, using a pseudo-random number generator, a parameter set comprising, for each adjustable anatomical parameter of the virtual model, a value of the corresponding provided range of values, while fulfilling the at least one relation; and a generating module configured to generate the virtual model of the virtual patient based on the template in the morphed state corresponding to the selected values of the adjustable anatomical parameters, AAPs.

The computing device may be realized as any device, or any means, for computing, in particular for executing a software, an App, or an algorithm. For example, a computing device may comprise at least one processing unit such as at least one central processing unit, CPU, and/or at least one graphics processing unit, GPU, and/or at least one field-programmable gate array, FPGA, and/or at least one application-specific integrated circuit, ASIC, and/or any combination of the foregoing. The computing device may further comprise a working memory operatively connected to the at least one processing unit and/or a non-transitory memory operatively connected to the at least one processing unit and/or the working memory. The computing device may be implemented partially and/or completely in a local apparatus (e.g., a personal computer, PC) and/or partially and/or completely in a remote system such as by a cloud computing platform.

A "virtual 3D mesh" in this context may be understood as a non-physical mesh object that contains information about positions and/or orientations of its constituent parts (e.g., mesh links) in a 3-dimensional space.

The virtual 3D mesh is preferably made from a healthy patient dataset or an available medical atlas model. In some advantageous embodiments, these 3D models are reconstructed from patient medical images (e.g. CT or MRI scans), through direct or indirect rendering methods. Preferably, one of two rendering methods is used: surface rendering (3D surface meshes with polygons) or point cloud rendering.

In the present context, "morphable" may mean that any or all constituent parts of the virtual 3D mesh can be non-elastically deformed, i.e. moved from their previous position according to the unmorphed state (or: unmorphed condition, or unmorphed configuration) of the template into a respective new position according to the morphed state (or: morphed condition, or morphed configuration) of the template.

Although care is taken to properly differentiate between the original morphable 3D mesh model, the template it is used as, the virtual model that is created (including morphing the template) and a graphical depiction of the virtual model, in many respects the differentiation is unnecessary and it will be readily appreciated how these objects are connected to one another.

The at least one relation may be a simply larger/smaller relation between one or more adjustable anatomical parameters, or it may be a function of at least two adjustable anatomical parameters, and/or a combination thereof. Preferably, the plausibility model is configured such as to provide a list of relations that ensure that a template in any morphed state (i.e. a virtual 3D mesh deformed from the "standard" configuration provided by the template module) that fulfills all of the relations of the list of relations (meaning, in other words, that the adjustable anatomical parameters associated with the particular morphed state of the template fulfill all of the relations) is a plausible virtual model of the human organ. Expressed differently, the generated virtual model advantageously able to pass as a model of an actual specimen of the organ in question.

The computer-implemented system may further comprise one or more database modules configured to store the morphable virtual 3D mesh, the range of values for each of the plurality of adjustable anatomical parameters and/or the at least one relation to be fulfilled by the template in the at least one morphed state. Advantageously, providing said morphable virtual 3D mesh, said range of values for each of the plurality of adjustable anatomical parameters and/or said at least one relation to be fulfilled by the template in the at least one morphed state may comprise receiving those values by the computing device from the at least one or more database modules.

The system may further comprise an output interface configured to output the generated virtual model to a recipient outside of the computer-implemented system, and may comprise equipment for a wireless or a wired connection to the recipient, such as a transmitter or transceiver or the like.

Although here, in the foregoing and in the following, some functions are described as being performed by modules, it shall be understood that this does not necessarily mean that such modules are provided as entities separate from one another. In cases where one or more modules are provided as software, the modules may be implemented by program code sections or program code snippets, which may be distinct from one another but which may also be interwoven.

Similarly, in case where one or more modules are provided as hardware, they functions of one or more modules may be provided by one and the same hardware component, or the functions of one module or the functions of several modules may be distributed over several hardware components which need not necessarily correspond to the modules one-to-one. Thus, any apparatus, system, method and so on which exhibits all of the features and functions ascribed to a specific module shall be understood to comprise, or implement, said module.

In particular, it is a possibility that all modules are implemented by program code executed by a computing device, e.g. a server or a cloud-computing platform.

In systems based on cloud computing technology, a large number of devices is connected to a cloud computing system via the Internet. The devices may be located in a remote facility connected to the cloud computing system. For example, the devices can comprise, or consist of, equipment, sensors, actuators, robots, and/or machinery in an industrial set-up(s). The devices can be medical devices and equipment in a healthcare unit. The devices can be home appliances or office appliances in a residential/commercial establishment.

The cloud computing system may enable remote configuring, monitoring, controlling, and maintaining connected devices (also commonly known as 'assets'). Also, the cloud computing system may facilitate storing large amounts of data periodically gathered from the devices, analyzing the large amounts of data, and providing insights (e.g., Key Performance Indicators, Outliers) and alerts to operators, field engineers or owners of the devices via a graphical user interface (e.g., of web applications). The insights and alerts may enable controlling and maintaining the devices, leading to efficient and fail-safe operation of the devices. The cloud computing system may also enable modifying parameters associated with the devices and issues control commands via the graphical user interface based on the insights and alerts.

The cloud computing system may comprise a plurality of servers or processors (also known as 'cloud infrastructure'), which are geographically distributed and connected to each other via a network. A dedicated platform (hereinafter referred to as 'cloud computing platform') is installed on the servers/processors for providing above functionality as a service (hereinafter referred to as 'cloud service'). The cloud-computing platform may comprise a plurality of software programs executed on one or more servers or processors of the cloud computing system to enable delivery of the requested service to the devices and its users.

One or more application programming interfaces (APIs) are deployed in the cloud computing system to deliver various cloud services to the users.

According to a second aspect of the present invention, a computer-implemented method for generating a virtual model of a virtual patient, comprising:

providing a morphable virtual 3D mesh as a template for a virtual model of at least a part of a human organ, providing a range of values for each of a plurality of adjustable anatomical parameters of the virtual model, each value associated with a corresponding morphed state of the template, providing at least one relation to be fulfilled by the template in at least one morphed state, the relation being between at least two of the plurality of adjustable anatomical parameters; and providing, using a pseudo-random number generator, a parameter set comprising, for each adjustable anatomical parameter of the virtual model, a value of the corresponding provided range of values, while fulfilling the at least one relation; and generating the virtual model of the virtual patient based on the template in the morphed state corresponding to the selected values of the adjustable anatomical parameters.

Additional advantageous embodiments, refinements, or variants of embodiments, will be apparent from the dependent claims as well as from the description in combination with the attached drawings.

In some advantageous embodiments, refinements, or variants of embodiments, the human organ is a human heart and the plurality of adjustable anatomical parameters, AAP, comprise at least one of:

a left coronary artery (LCA) distance;

a right coronary artery (RCA) distance;

an aorta diameter;

a size of the aortic annulus;

a sinotubular (ST) junction height;

a calcification form of a leaflet of a heart valve;

a pose of a heart valve;

an opening percentage of a heart valve;

a heart valve diameter;

a leaflet effective height;

a ventriculo-aortic (VA) junction height; and/or a leaflet basal ring diameter.

In particular, the LCA and RCA distance can be measured with respect to a specific other structure within the human heart, e.g., to a specific valve annulus like the tricuspid valve annulus.

These adjustable anatomical parameters, AAP, have been found by the inventor to be both easily implementable in the morphable virtual 3D mesh as well as impactful on plausibility and usefulness of the virtual model itself.

Here and in the following, for some (especially longer) terms abbreviations (such as "AAP" for "adjustable anatomical parameter", or abbreviations or acronyms for certain of the modules) are used. Usually, the terms will be given followed by the corresponding abbreviations. In some cases, to improve legibility, only the abbreviation will be used, whereas in other cases only the term itself will be used. In all cases, the term itself and the corresponding abbreviation shall be understood to be equivalent.

In some advantageous embodiments, refinements, or variants of embodiments, the computing device is further configured to implement a graphics module, GRAM, configured to generate a graphical representation of at least the generated virtual model. The graphical representation may be displayed by a display, which may be part of the system or which may be external to the system. The graphical representation may, for example, be used for teaching physicians or other medicals professionals. It may also be used, for example, in an automated test, where tested persons (e.g., students of Medicine) are automatically shown graphical representations of pre-generated, or even live-generated, virtual models, and may have to register an assessment or a comment, which can later be analyzed by a professional (e.g., a teacher of Medicine), for example for grading.

The graphical representation may comprise other graphical elements not part of the virtual model, for example visual indications of a particular disease or other physiological condition, alphanumerical pieces of information, and/or the like.

In some advantageous embodiments, refinements, or variants of embodiments, the graphical representation further comprises an indication of a value of at least one adjustable anatomical parameter, AAP. For example, in the case of a human heart, an opening percentage of a heart valve may be indicated as a number, together with its depicting in the graphical representation. Preferably, the indication of the value is in each case depicted together with a corresponding indication of how said value is located within the corresponding range of values for said adjustable anatomical parameter, AAP.

In some advantageous embodiments, refinements, or variants of embodiments, the indication of how said value is located within the corresponding range of values for said adjustable anatomical parameter, AAP, is realized by the graphical representation depicting a slider graphics object (e.g., a float slider). The slider graphics object may comprise a sliding bar and a sliding body movable along within the sliding bar, wherein the extent of the sliding bar represents the range of values, and a position of the sliding body represents the size of the value compared to the range of values. This provides an objectively improved display of information to a user, who not only at a glance realizes the impact the value has on the virtual model but also intuitively grasps how large this values is with respect to all other possible values.

In some advantageous embodiments, refinements, or variants of embodiments, the system further comprises a graphical user interface, GUI, enabling a user to interact with the generated graphical representation.

In particular, the graphical user interface, GUI, may further enable the user to make manual changes to the value of at least one adjustable anatomical parameter, AAP, wherein the GUI is configured to display a result of the manual changes graphically to the user. To this end, the change made (or: requested) by the user may be fed to the generating module, which re-generates the virtual model based on the changed set of parameters. The graphics module may generate a new corresponding graphical representation, which is then displayed by the graphical user interface.

In some advantageous embodiments, refinements, or variants of embodiments, the computing device is further configured to implement a physiology module, PHYM, configured to run a mathematical simulation of the physiology of the virtual patient corresponding to the virtual model. The adjustable anatomical parameters, AAPs, of the list of adjustable anatomical parameters, AAP, given above can strongly effect the physiological processes simulated by the physiology engine for a human heart and therefore improve its output.

In some advantageous embodiments, refinements, or variants of embodiments, the graphics module, GRAM, is further configured to generate the graphical representation with a virtual environment comprising the generated virtual model. Advantageously, the graphical representation also comprises features indicating at least one physiological property of the virtual patient based on the mathematical simulation of the physiology of the virtual patient.

In some advantageous embodiments, refinements, or variants of embodiments, the anatomical parameters module, APM, is configured to access a medical database and to determine the range of values for at least one of the plurality of adjustable anatomical parameters therefrom automatically. The medical database may be, for example, a repository of medical scientific literature, a medical encyclopedia, a Picture Archiving and Communication System, PACS, a hospital patient record system, and/or the like. The anatomical parameters module, APM, may also be configured to check periodically for updates of the ranges of values, and/or may be configured to receive push messages indicating updates and to re-determine, as a reaction, at least one of the ranges of values. In this way, the ranges of parameter values are kept updated.

Similarly, the plausibility module may be configured to automatically access a medical database (the same as the anatomical parameters module, APM, or a different one) in order to look for updates of the at least one relation between the plurality of adjustable anatomical parameters, AAP. In this way, for example, new medical findings of relations between different anatomical features, expressed by the adjustable anatomical parameters, AAP, can quickly be incorporated into the system.

In some advantageous embodiments, refinements, or variants of embodiments, the morphable virtual 3D mesh is surface-rendered. In surface rendering, first a volume data is gathered, e.g. from a medical imaging dataset or a real patient. Afterwards, using a surface generation algorithm (e.g. "marching cubes" published in the 1987 SIGGRAPH proceedings by Lorensen et al., or tetrahedra) a polygon-based surface is generated that represents the surface of the real patient's volume data. These polygons are representing a surface enclosed by a minimum number of three vertices (a triangle). Each one of these vertices contribute to the shape of the generated polygon and, in turn, the whole surface mesh.

The morphable virtual 3D mesh may be morphed (i.e. brought into a morphed state) via manipulating these vertices, for example via per-vertex displacement approaches such as the ones described in "Szirmay-Kalo/Umenhoffer" as cited above, which describes "displacement mapping algorithms", and which is hereby incorporated in its entirety by reference. In this way, one can change the shape of the originally generated mesh in a highly detailed manner. Accordingly, the morphed state of the template can be determined precisely, which, in turn, may enable a physiology engine to run its simulation especially accurately, for example.

In some advantageous embodiments, refinements, or variants of embodiments, the morphable virtual 3D mesh is point-cloud rendered, for example according to any of the known methods described in "Kivi et al.", which is hereby incorporated in its entirety by reference.

In some advantageous embodiments, refinements, or variants of embodiments, of the method for generating a training data set for machine learning, the generated training samples are automatically labelled based on the respective parameter set used to generate the virtual model of each training sample. For example, the label may simply be the value of one particular adjustable anatomical parameter, AAP.

It shall be understood that the method according to the second aspect of the present invention may be used with the system according any embodiment of the first aspect of the present invention. Therefore, any variants, options, or refinements described with respect to the system according to the first aspect may be equally applied to the method according to the second aspect of the present invention and vice versa. For the sake of brevity, therefore, mainly the different modules and functions of the system will be described, and it shall be understood that the methods taught herein may be adapted to perform any of the functions described therein.

According to a third aspect, the invention provides a computer program product comprising executable program code configured to, when executed by a computing device, perform the method according to any embodiment of the second aspect of the present invention.

According to a fourth aspect, the invention provides a non-transient computer-readable data storage medium comprising executable program code configured to, when executed by a computing device, perform the method according to any embodiment of the second aspect of the present invention.

The non-transient computer-readable data storage medium may comprise, or consist of, any type of computer memory, in particular semiconductor memory such as a solid-state memory. The data storage medium may also comprise, or consist of, a CD, a DVD, a Blu-Ray-Disc, an USB memory stick or the like.

According to a fifth aspect, the invention provides a data stream comprising, or configured to generate, executable program code configured to, when executed, perform the method according to any embodiment of the second aspect of the present invention.

According to a sixth aspect, the invention provides a computer-readable medium storing data which defines both the virtual model of the virtual patient and operating instructions adapted to control an additive manufacturing device to fabricate a physical model of the virtual patient using the virtual model when said data is relayed to the additive manufacturing device. Thus, the virtual model may be used to produce a physical model that can be used in teaching physicians, in training surgeons and the like.

The invention will be explained in greater detail with reference to exemplary embodiments depicted in the drawings as appended.

Although specific embodiments have been illustrated and described herein, it will be appreciated by those of ordinary skill in the art that a variety of alternate and/or equivalent implementations may be substituted for the specific embodiments shown and described without departing from the scope of the present invention. Generally, this application is intended to cover any adaptations or variations of the specific embodiments discussed herein.

FIG. 1 shows a schematic block diagram illustrating a system 1000 for generating a virtual model of a virtual patient according to an embodiment of the present invention.

The system 1000 comprises a computing device 100 configured to implement several modules.

The computing device 100 is configured to implement a template module 110 configured to provide a morphable virtual 3D mesh as a template for a virtual model of at least a part of a human organ. Although in the following example embodiments will be described with respect to a human heart as the human organ, it shall be understood that the invention may equally be applied to any other kind of organ as well.

Figure 2:
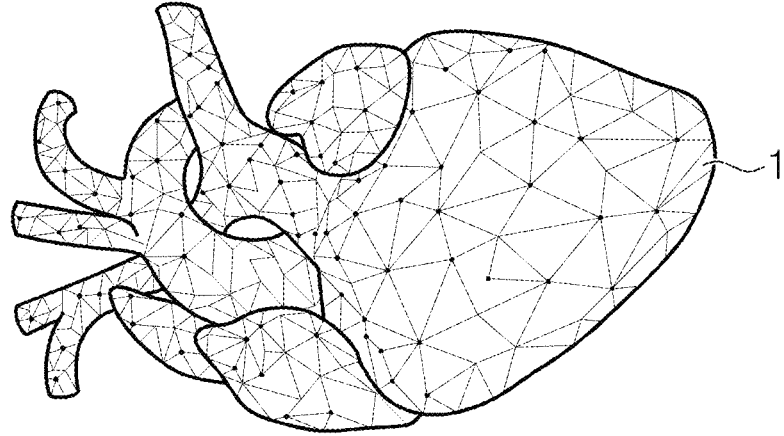
FIG. 2 a schematic diagram of a morphable virtual 3D mesh of a human heart for use in the system of FIG. 1.

FIG. 2 shows a schematic diagram of a morphable virtual 3D mesh 1 of a human heart.

As has been described in the foregoing, the morphable virtual 3D mesh may be rendered using any known rendering technique, in particular using surface rendering or point-cloud rendering as described in "Szirmay-Kalo/Umenhoffer" and "Kivi et al.".

The morphability of the virtual 3D mesh model 1 used as template may be realized as follows:

An originally generated model is imported into a 3D design software with per-vertex animation capability.

For each determined feature expressible by an adjustable anatomical parameter, AAP, a copy of the original mesh is made.

On the copied version, the group of vertices that represent the feature, is selected, and manipulated until an extreme end of the range of values for that AAP is reached, for example until (reasonably) maximum observed values reported in the medical literature is achieved.

Using the per-vertex animation functionality, the vertices position differential between the original and the copy is stored as a value, specific to that vertices group.

Already at this stage, the values of the AAP may be represented as a float slider, the sliding bar of which indicates the range of values. Each position on the float slider (or, in other words, each value of the AAP) corresponds to an interpolation between the original mesh in the unmorphed state, and the copy mesh in the morphed state. Each point on the float slider thus provides a new variability.

These steps may be repeated until all the determined key features are implemented in the virtual model.

In these steps, per-vertex animation techniques such as IKA Morph target animation, shape interpolation, shape keys, or blend shapes may be used. A pseudo-randomised algorithm would create a new patient anatomy by generating the defined morph values.

The computing device 100 is further configured to implement an anatomical parameters module, APM 120, configured to provide a range of values for each of a plurality of adjustable anatomical parameters, AAP, of the virtual model, each value associated with a corresponding morphed state of the template, i.e. of the original virtual 3D mesh.

For example, the anatomical parameters module, APM 120, is configured to access a medical database 300 and to automatically determine the range of values for at least one of the plurality of adjustable anatomical parameters therefrom, such as by crawling through a repository of scientific medical knowledge.

The computing device 100 is further configured to implement a plausibility module 130 configured to provide at least one relation to be fulfilled by the template in at least one morphed configuration, the relation being between at least two of the plurality of adjustable anatomical parameters, AAP. Preferably, a plurality of relations (which may include one or more functions) may be provided by the plausibility module 130. The relations may be stored in a dedicated data storage of the plausibility module 130, or in a common data storage 190 of the computing device 100 (as shown in FIG. 1) or of the system 1000.

The computing device 100 is further configured to implement an instantiation module 140 configured to provide, using a pseudo-random number generator 141, a parameter set comprising, for each adjustable anatomical parameter of the virtual model, a value of the corresponding provided range of values, while fulfilling the at least one relation. For example, the instantiation module 140 may be configured to first evaluate the relations provided by the plausibility module 130 and to determine therefrom a/the adjustable anatomical parameter, AAP, with the fewest restrictions, preferably with no restrictions. The value range for that adjustable anatomical parameter, AAP, provided by the anatomical parameters module, APM 120, is then mapped onto a numerical interval, such as from 0 (included) to 1 (included), in which the pseudo-random number generator 141 is configured to generate random numbers. Thus, each generated random number corresponds to a value of the adjustable anatomical parameter within its allowed value range.

The same may be done for each other adjustable anatomical parameter as well, preferably following a hierarchy of adjustable anatomical parameters, AAPs, from the ones with the lowest number of restrictions to the ones with the highest number of restrictions. In each case, the value range provided by the anatomical parameters module, APM 120, may amended such that only values that fulfill the restrictions according to the relations, based on the already randomly determined values are allowed. The amended value range may be shortened at one end or the other or both, and/or it may comprise disallowed areas in the middle. In any case, the remaining allowed values are again mapped on the numerical interval, and the process is continued. Should there be no allowable values left, the instantiation module 140 may be configured to go back a specific number of steps (e.g. one step, two steps, three or more steps, or all steps) of randomly determining values, and re-start from there. This may be continued until allowable values have been found for all adjustable anatomical parameters, AAPs.

The mapping of the range of values onto the numerical interval may be done as a linear 1-to-1 correspondence, or it may be done according to statistical likelihood. For example, the anatomical parameters module, APM 120, may not only provide the ranges of the values for the adjustable anatomical parameters, AAPs, but it may also provide an information about the likelihood of the values within the ranges, or, expressed differently, a probability distribution of the values within their respective range.

The mapping may follow this probability distribution, so that during instantiation by the instantiation module 140, i.e., when the parameter set for one particular virtual model is generated, on average values with a probability value of x % will be selected y times as often as values with a probability value of x/y %. This has the effect that the generated virtual models are not only plausible each in their own right in that they could exist in reality, but that the distribution of parameter sets over several virtual models also is plausible. In other words, virtual models with extreme configurations due to extreme values for the adjustable anatomical parameters, AAPs, will be less common than virtual models with more moderate configurations.

The computing device 100 may allow different settings, for example, one mode in which the range of values is mapped as a linear 1-to-1-correspondence onto the numerical interval, and another mode in which the mapping is performed according to the information about the likelihood of the values within the ranges. The former mode may be useful for teaching students how to recognize or deal with extreme cases, whereas the latter mode may be useful for training students on a distribution of virtual models that is more similar to one they might actually encounter in reality. The same is true for using the generated virtual models for the training of artificial intelligence entities. The former mode will produce more different training samples, enabling the artificial intelligence entities to deal with all kinds of anatomical situations. The latter mode may help dealing with overfitting and may bias the artificial intelligence entities to correctly deal with the larger number of more probable configurations.

The computing device 100 is further configured to implement a generating module 150 configured to generate the virtual model of the virtual patient based on the template in the morphed state corresponding to the selected values of the adjustable anatomical parameters, AAPs.

The computing device 100 is further configured to implement a graphics module, GRAM 170, configured to generate a graphical representation of at least the generated virtual model.

Figure 3:
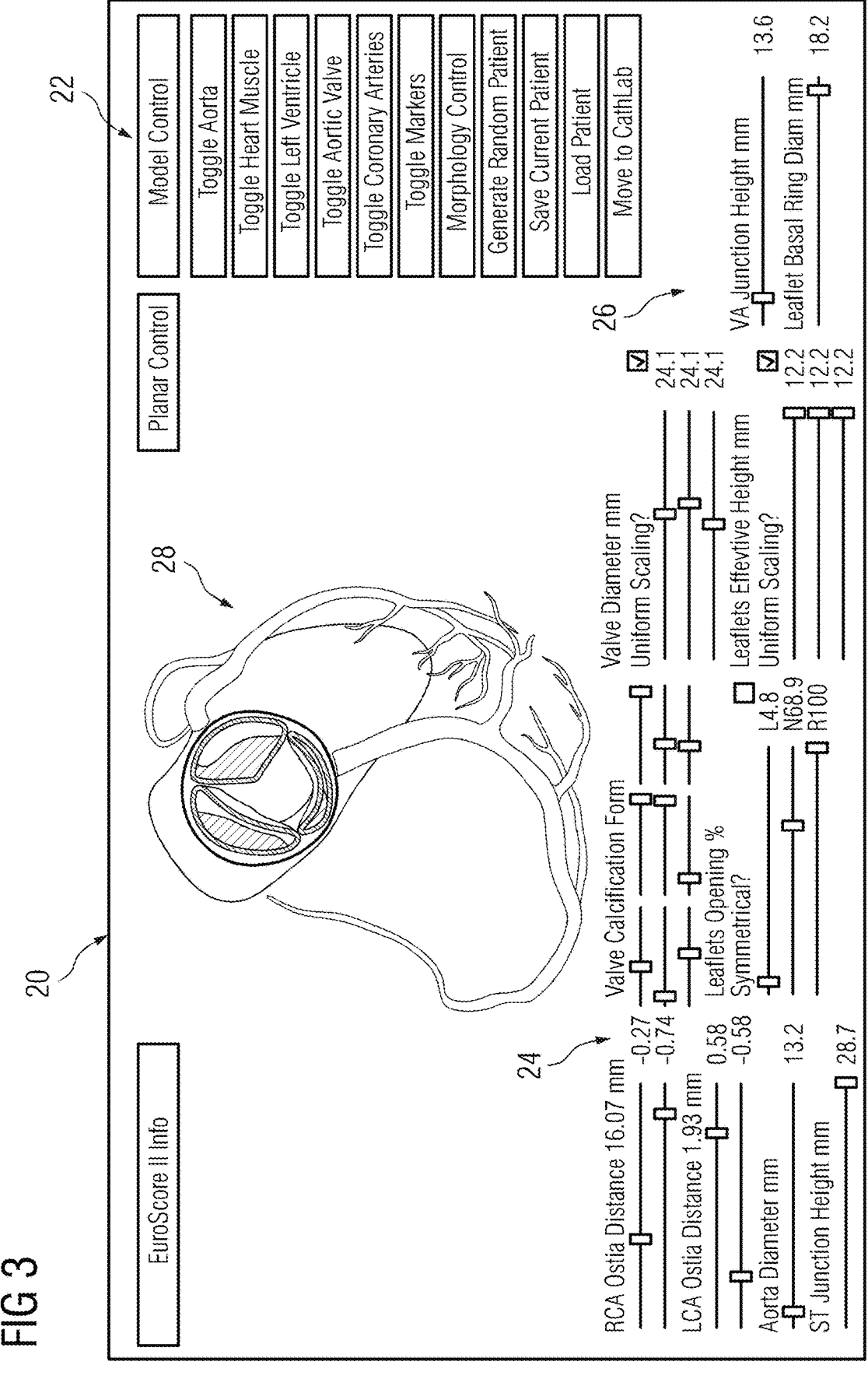
FIG. 3 shows an exemplary graphical representation as it may be generated by the system of FIG. 1.

FIG. 3 shows an exemplary depiction of a graphical representation 20. The system 1000 may comprise a graphical user interface, GUI 180, displayed by a display device 200, a touch screen, a mobile device screen and/or the like, which may also be part of the system 1000.

The graphical representation 20 may comprise, apart from the generated virtual model, a control interface 22 and/or indications 24, for at least one adjustable anatomical parameter, of the value used for it to generate the virtual model, and preferably also an indication of how said value is located within the corresponding range of values for said adjustable anatomical parameter, AAP.

Advantageously, the indications are, as shown in FIG. 3, realized with slider graphics object (here: floating sliders 26). The position of the sliding body within the sliding bar represents the magnitude of the value with respect to the allowed range of values for it. In addition, the selected value is also display numerically.

In this way, a user 2 viewing the graphical representation 20 may intuitively understand, for example, that the graphical depiction 28 of the virtual model is based on a parameter set wherein the leaflet basal ring diameter is 18.2 mm, and will also intuitively understand, from the corresponding slider graphics object 26, that this is among the highest possible values for said diameter.

Moreover, just by briefly glancing at the graphical representation 20, the user 2 can objectively faster and easier acquire the information whether the depicted virtual model is rather a typical specimen (in which case the sliding bodies would all be about the center of their sliding bars) or whether a specimen is shown that is atypical in one or more adjustable anatomical parameters, AAPs.

The instantiation of a particular virtual model may be performed by the instantiation module 140 in real time (or quasi-real time) while the graphical representation 20 is being displayed. For example, the graphical representation 20 may first show a depiction of the original template, i.e., the morphable virtual 3D mesh in its unmorphed state, and a user interaction prompt (e.g., a button in the graphical user interface, GUI 180) which triggers an instantiation by the instantiation module 140 and a corresponding morphing of the depicted virtual 3D mesh. The user interaction prompt may persist so that the user 2 may repeatedly request new instantiations. In this way, a teacher may show students a large variety of plausible human organs one after the other, discussing possible issue, treatments and so on without any participant having knowledge of the organs that are going to be displayed.

The graphical user interface, GUI 180, may be configured to allow the user 2 manual changes to any or all adjustable anatomical parameters, AAPs. In preferred embodiments, this is subject to the condition of fulfilment of the relations provided by the plausibility module 130, in other embodiments, the user 2 is free to make any desired changes. In some embodiments, the graphical user interface, GUI 180, may allow a user to switch between a first mode, in which the manual change of AAPs is subject to the condition of fulfilment of the relations provided by the plausibility module 130, and a second mode, in which any change is allowed.

As an example, a user 2 wishing to evaluate whether a particular instrument will be small enough to be used with a large number of patients, may introduce a graphical depiction of the instrument into the graphical representation 20, and change one or more values of adjustable anatomical parameters, AAPs, such that the instrument is able to be used, for example, able to enter a particular blood vessel. The user 2 will then see the corresponding changes to the virtual model according to the relations provided by the plausibility module 130 entail. The user 2 will also see how "normal" the chosen values of the AAPs are with respect to their respective range, and so gain an immediate intuitive grasp on how likely it is that said particular instrument will be usable for a large number of patients.

Similarly, the system 1000 may comprise an evaluation module 210 configured to receive at least one condition from the user 2, and either a set of virtual models or, preferably, a number of virtual models to be generated by the system 1000 as described in the foregoing. The evaluation module 210 may then automatically instruct the computing device 100 to generate said number of virtual models, and may provide the user 2 with a result about the compliance of the virtual models with the at least one condition. For example, the evaluation module 210 may inform the user about how many of the generated virtual models fulfil the at least one condition, about a median, a variance and/or other statistical variables of the generated virtual models with respect to the at least one condition. Since the allowable parameters are given by the anatomical parameters module, APM 120, and the plausibility module 130, a large number of generated virtual model may yield similar results as a large and incredibly involved study of the same number of actual human organs would yield.

As mentioned above, the graphical user interface, GUI 180, may be configured to allow the user 2 to make only such manual changes that fulfill all of the relations provided by the plausibility module 130 and/or to automatically adjust other adjustable anatomical parameters, AAPs, so that all of the relations provided by the plausibility module 130 are fulfilled despite the manual changes by the user 2. Adjustable anatomical parameters, AAPs, that are automatically adjusted in this way may be displayed to the user in an intuitive way, for example by changing graphical slider objects of the graphical representation accordingly, optionally indicating the changes by differences markers, color changes, and/or the like.

The computing device 100 may further be configured to implement a physiology module, PHYM 160, configured to run a mathematical simulation of the physiology of the virtual patient corresponding to the virtual model.

The graphics module, GRAM 170, may further be configured to generate the graphical representation 20 with a virtual environment comprising the depiction 28 of the generated virtual model, wherein the graphical representation 20 also comprises features indicating at least one physiological property of the virtual patient based on the mathematical simulation of the physiology of the virtual patient.

Figure 4:
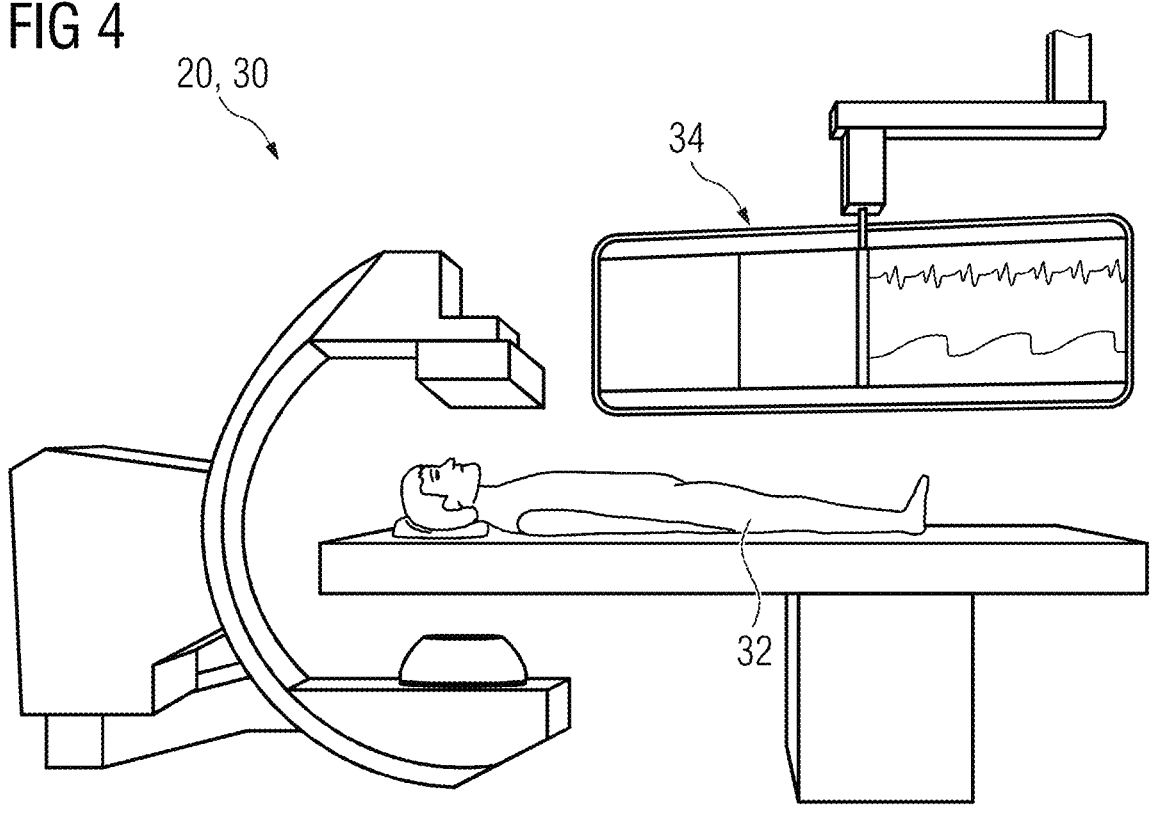
FIG. 4 schematically shows another exemplary graphical representation as it may be generated by the system of FIG. 1.

FIG. 4 schematically shows a graphical representation 20 comprising a virtual environment 30 containing a depiction 32 of a virtual patient as well as features 34 indicating physiological properties of the virtual patient such as heartbeat, blood pressure, oxygenation and so on. The virtual environment 30 in FIG. 4 is designed as a virtual operating room. A user 2 may be able to see the depiction 28 of the generated virtual model within a depiction 32 of the virtual patient, together with the features 34, and may thus experience a situation much as it would be in reality. The graphical user interface, GUI 180, the graphical representation 20, the virtual environment 30 and so on may all be used on a display, but also in augmented reality, AR, or virtual reality, VR, applications. Thus, the graphics module, GRAM 170, may be configured to generate the graphical representation 20 as an AR or a VR graphical representation.

Figure 5:
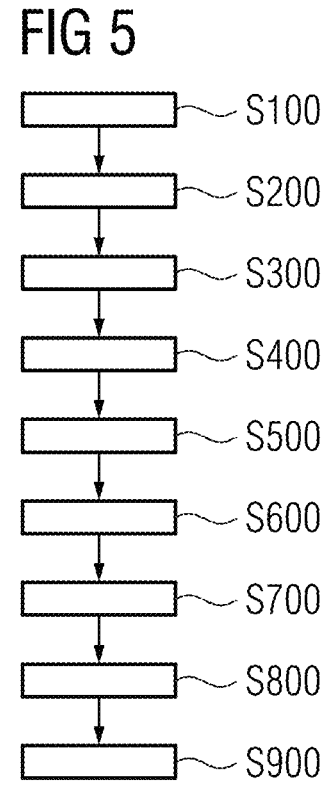
FIG. 5 shows a schematic flow diagram illustrating a method according to an embodiment of the present invention, i.e., a computer-implemented method for generating a virtual model of a virtual patient.

FIG. 5 shows a schematic flow diagram illustrating a method according to an embodiment of the second aspect of the present invention, i.e., a computer-implemented method for generating a virtual model of a virtual patient.

The method of FIG. 5 may be used with the system 1000 as explained with respect to FIGS. 1 to 4, but also separately therefrom. Accordingly, all options, variants and refinements described for the system according to the first aspect of the present invention, in particular to the system 1000, are equally applicable to the method of FIG. 5, and vice versa.

In a step S100, a morphable virtual 3D mesh is provided as a template for a virtual model of at least a part of a human organ, for example as has been described in the foregoing with respect to the template module 110.

In a step S200, a range of values for each of a plurality of adjustable anatomical parameters of the virtual model is provided, each value associated with a corresponding morphed state of the template, for example as has been described in the foregoing with respect to the anatomical parameters module 120.

In a step S300, at least one relation to be fulfilled by the template in at least one morphed state is provided, the relation being between at least two of the plurality of adjustable anatomical parameters, for example as has been described in the foregoing with respect to the plausibility module 130.

In a step S400 (in particular using a pseudo-random number generator), a parameter set comprising, for each adjustable anatomical parameter of the virtual model, a value of the corresponding provided range of values, while fulfilling the at least one relation, is provided, for example as has been described in the foregoing with respect to the instantiation module 140.

In a step S500, the virtual model of the virtual patient is generated based on the template in the morphed state corresponding to the selected values of the adjustable anatomical parameters, for example as has been described in the foregoing with respect to the generating module 150.

Further steps may comprise any or all of:

a step S600 of running a mathematical simulation of the physiology of the virtual patient corresponding to the virtual model, for example as has been described in the foregoing with respect to the physiology module, PHYM 160;

a step S700 of generating a graphical representation of at least the generated virtual model, i.e. a graphical representation including at least a graphical depiction 28 of the generated virtual model;

a step S800 of receiving manual changes by a user 2, for example as has been described with respect to the graphical user interface, GUI 180, in the foregoing, and of adapting the virtual model and/or the graphical representation 20 in accordance with the received manual changes, preferably together with graphically displaying a result of the manual changes to the user 2; and/or a step S900 of automatically accessing a medical database to automatically determine the ranges of values for at least one of the plurality of adjustable anatomical parameters, AAPs, for example as has been described in the foregoing with respect to the anatomical parameters module, APM 120.

The present invention also provides a computer-implemented method for generating a training data set for machine learning, comprising generating N training samples by generating at least N virtual models according to the method of any embodiment of the second aspect of the present invention. This method of generating a training data set may also comprise a step of automatically labelling the generated training samples based on the respective parameter set used to generate the virtual model of each training sample. For example, the label may simply be the value of one particular adjustable anatomical parameter, AAP.

Figure 6:
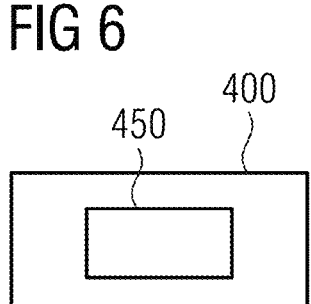
FIG. 6 shows a computer program product according to another embodiment of the present invention.

FIG. 6 shows a schematic block diagram illustrating a computer program product 400 according to an embodiment of the fourth aspect of the present invention. The computer program product 400 comprises executable program code 450 configured to, when executed, perform the method according to any embodiment of the second aspect of the present invention in particular as has been described with respect to the preceding figures.

Figure 7:
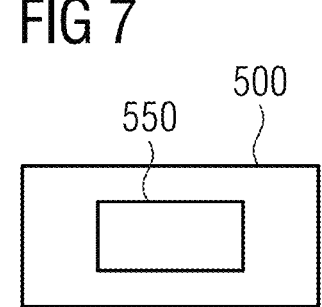
FIG. 7 shows a data storage medium according to yet another embodiment of the present invention.

FIG. 7 shows a schematic block diagram illustrating a non-transitory computer-readable data storage medium 500 according to an embodiment of the fifth aspect of the present invention. The data storage medium 500 comprises executable program code 550 configured to, when executed, perform the method according to any embodiment of the second aspect of the present invention, in particular as has been described with respect to the preceding figures.

The non-transient computer-readable data storage medium may comprise, or consist of, any type of computer memory, in particular semiconductor memory such as a solid-state memory. The data storage medium may also comprise, or consist of, a CD, a DVD, a Blu-Ray-Disc, an USB memory stick or the like.

Independent of the grammatical term usage, individuals with male, female or other gender identities are included within the term.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The invention claimed is:

1. A computer-implemented system for generating a virtual model of a virtual patient, comprising:
   a computing device configured to cause the system to,
   provide a morphable virtual 3D mesh as a template for a virtual model of at least a part of a human organ;
   provide a range of values for each of a plurality of adjustable anatomical parameters of the virtual model, each value associated with a corresponding morphed state of the template;
   provide at least one relation to be fulfilled by the template in at least one morphed state, the relation being between at least two of the plurality of adjustable anatomical parameters;
   provide, using a pseudo-random number generator, a parameter set comprising, for each adjustable anatomical parameter of the virtual model, a value of the corresponding provided range of values, while fulfilling the at least one relation; and
   generate the virtual model of the virtual patient based on the template in the morphed state corresponding to the provided values of the adjustable anatomical parameters generated by the pseudo-random number generator.

2. The system of claim 1, wherein the human organ is a human heart and the plurality of adjustable anatomical parameters comprise at least one of:
   a left coronary artery distance;
   a right coronary artery distance;
   an aorta diameter;
   a size of a aortic annulus;
   a sinotubular junction height;
   a calcification form of a leaflet of a heart valve;
   a pose of a heart valve;
   an opening percentage of a heart valve;
   a heart valve diameter;
   a leaflet effective height;
   a ventriculo-aortic junction height; or
   a leaflet basal ring diameter.

3. The system of claim 2, wherein the computing device is further configured to cause the system to generate a graphical representation of at least the generated virtual model.

4. The system of claim 1, wherein the computing device is further configured to cause the system to generate a graphical representation of at least the generated virtual model.

5. The system of claim 4, wherein the graphical representation further comprises an indication of a value of at least one adjustable anatomical parameter in each case together with a corresponding indication of how the value is located within the corresponding range of values for the adjustable anatomical parameter.

6. The system of claim 5, wherein the indication of how the value is located within the corresponding range of values for the adjustable anatomical parameter is realized by the graphical representation depicting a slider graphics object comprising a sliding bar and a sliding body movable along within the sliding bar, wherein an extent of the sliding bar represents the range of values, and a position of the sliding body represents a size of the value compared to the range of values.

7. The system of claim 4, further comprising:
   a graphical user interface enabling a user to interact with the generated graphical representation.

8. The system of claim 7, wherein the graphical user interface further enables the user to make manual changes to the value of at least one adjustable anatomical parameter and wherein the graphical user interface is configured to graphically display a result of the manual changes to the user.

9. The system of claim 8, wherein the computing device is further configured to cause the system run a mathematical simulation of a physiology of the virtual patient corresponding to the virtual model.

10. The system of claim 9, wherein the computing device is further configured to cause the system to generate the graphical representation with a virtual environment comprising a depiction of the generated virtual model, wherein the graphical representation also comprises features indicating at least one physiological property of the virtual patient based on the mathematical simulation of the physiology of the virtual patient.

11. The system of claim 4, wherein the computing device is further configured to cause the system to generate the graphical representation with a virtual environment comprising a depiction of the generated virtual model, wherein the graphical representation also comprises features indicating at least one physiological property of the virtual patient based on a mathematical simulation of a physiology of the virtual patient.

12. The system of claim 11, wherein the computing device is further configured to cause the system to access a medical database and to automatically determine the range of values for at least one of the plurality of adjustable anatomical parameters therefrom.

13. The system of claim 1, wherein the computing device is further configured to cause the system to access a medical database and to automatically determine the range of values for at least one of the plurality of adjustable anatomical parameters therefrom.

14. The system of claim 1, wherein the morphable virtual 3D mesh is surface rendered or point-cloud rendered.

15. A computer-implemented method for generating a virtual model of a virtual patient, comprising:
   providing a morphable virtual 3D mesh as a template for a virtual model of at least a part of a human organ;
   providing a range of values for each of a plurality of adjustable anatomical parameters of the virtual model, each value associated with a corresponding morphed state of the template;

providing at least one relation to be fulfilled by the template in at least one morphed state, the relation being between at least two of the plurality of adjustable anatomical parameters;

providing, using a pseudo-random number generator, a parameter set comprising, for each adjustable anatomical parameter of the virtual model, a value of the corresponding provided range of values, while fulfilling the at least one relation; and generating the virtual model of the virtual patient based on the template in the morphed state corresponding to the provided values of the adjustable anatomical parameters from the pseudo-random number generator.

16. A computer-implemented method for generating a training data set for machine learning, comprising generating N training samples by generating at least N virtual models according to the method of claim 15.

17. A non-transitory, non-volatile, computer-readable data storage medium comprising executable program code, when executed by a computing device, cause the computing device to perform the method of claim 15.

\* \* \* \* \*